US012636418B2

(12) United States Patent
Gipson

(10) Patent No.: US 12,636,418 B2
(45) Date of Patent: **\*May 26, 2026**

(54) SYSTEM AND METHOD FOR REDUCING GASEOUS MICROEMBOLI USING VENOUS BLOOD BYPASS WITH FILTER

(71) Applicant: Keith Gipson, Wallingford, CT (US)

(72) Inventor: Keith Gipson, Wallingford, CT (US)

( \* ) Notice: Subject to any disclaimer, the term of this patent is extended or adjusted under 35 U.S.C. 154(b) by 783 days.

This patent is subject to a terminal disclaimer.

(21) Appl. No.: 17/948,691

(22) Filed: Sep. 20, 2022

(65) Prior Publication Data

US 2023/0044772 A1 Feb. 9, 2023

Related U.S. Application Data

(63) Continuation of application No. 16/322,513, filed as application No. PCT/US2017/044573 on Jul. 31, 2017, now Pat. No. 11,452,804.

(60) Provisional application No. 62/369,262, filed on Aug. 1, 2016.

(51) Int. Cl.
A61M 1/36 (2006.01)
A61M 1/16 (2006.01)

(52) U.S. Cl.
CPC ........ A61M 1/3627 (2013.01); A61M 1/1698 (2013.01); A61M 1/3623 (2022.05); A61M 1/3666 (2013.01); *A61M 2205/3334* (2013.01); *A61M 2205/75* (2013.01); *A61M 2205/7545* (2013.01)

(58) Field of Classification Search
CPC ........... A61M 1/36276; A61M 1/1698; A61M 1/3666; A61M 3305/75
See application file for complete search history.

(56) References Cited

U.S. PATENT DOCUMENTS

| | | | |
|---|---|---|---|
| 4,572,724 A | 2/1986 | Rosenberg et al. | |
| 5,976,463 A | 11/1999 | Nomura et al. | |
| 11,452,804 B2 * | 9/2022 | Gipson ............... | A61M 1/1698 |
| 2012/0277654 A1 | 11/2012 | Olson et al. | |
| 2013/0004369 A1 | 1/2013 | Marseille | |
| 2013/0296633 A1 | 11/2013 | Strueber | |
| 2016/0015881 A1 | 1/2016 | Utsugida et al. | |

FOREIGN PATENT DOCUMENTS

| | | |
|---|---|---|
| JP | H09504205 A | 4/1997 |
| JP | H10127761 A | 5/1998 |
| JP | 2016019667 A | 2/2016 |
| WO | 9719714 A1 | 6/1997 |
| WO | 02064013 A2 | 8/2002 |

(Continued)

OTHER PUBLICATIONS

Extended European Search Report for EP Application No. 23205357.9; Report mail date Apr. 8, 2024 (13 pages).

(Continued)

*Primary Examiner* — Leslie R Deak
(74) *Attorney, Agent, or Firm* — CANTOR COLBURN LLP

(57) ABSTRACT
A system and method for reducing gas bubbles, including gaseous microemboli (GME) during cardiopulmonary bypass (CPB) by the use of an oxygenator with venous blood bypass and a filter in the venous blood bypass is provided.

20 Claims, 7 Drawing Sheets

(56) References Cited

FOREIGN PATENT DOCUMENTS

| WO | 03066134 | A1 | 8/2003 |
| WO | 2015047927 | A1 | 4/2015 |

OTHER PUBLICATIONS

International Search Report mailed Oct. 13, 2017; International Application No. PCT/US17/44573; International Filing Date Jul. 31, 2017 (10 pages).

Written Opinion mailed Oct. 13, 2017; International Application No. PCT/US17/44573; International Filing Date Jul. 31, 2017 (7 pages).

* cited by examiner

SWEEP GAS OUTLET

WATER CONNECTIONS FOR HEAT EXCHANGER

BLOOD OUTLET

SWEEP GAS OUTLET MANIFOLD (CONTAINING VENT OPENINGS)

OXYGENATOR FIBER BUNDLE

SWEEP GAS INLET MANIFOLD

SWEEP GAS INLET

OXYGENATOR HOUSING

BLOOD INLET

CONDITION 1 - VENOUS BLOOD FROM PATIENT SIMULATOR
CONDITION 2 - ARTERIAL BLOOD FROM HEART-LUNG MACHINE WITH
              FILTERED SHUNT IN PLACE
CONDITION 3 - ARTERIAL BLOOD FROM HEART-LUNG MACHINE WITH
              NO SHUNT
Y-AXES ARE PARTIAL PRESSURES OF DISSOLVED $CO_2$ OR $O_2$ IN mmHg

CONTROL = NO SHUNT
FILTERED = FILTERED SHUNT
Y-AXES ARE EMBOLI PER MINUTE
X-AXES ARE EMBOLI DIAMETER IN MICROMETERS

CONTROL = NON-FILTERED SHUNT
FILTERED = FILTERED SHUNT
Y-AXES ARE EMBOLI PER MINUTE
X-AXES ARE EMBOLI DIAMETER IN MICROMETERS

SYSTEM AND METHOD FOR REDUCING GASEOUS MICROEMBOLI USING VENOUS BLOOD BYPASS WITH FILTER

CROSS REFERENCE TO RELATED APPLICATION

This application is a continuation application of application Ser. No. 16/322,513, filed Feb. 1, 2019, which is a 371 of International Application No. PCT/US2017/044573, filed Jul. 31, 2017 which claims priority to and the benefit of U.S. provisional patent application Ser. No. 62/369,262, filed on Aug. 1, 2016, the contents of which is included herein by reference in their entireties.

FIELD

The disclosure relates to a system and method for cardiopulmonary bypass, and more particularly to a system and method to reduce gaseous microemboli (GME) using an oxygenator with venous bypass and a filter.

BACKGROUND

There is a need to replace the function of the heart and lungs by artificial means, such as during heart operations. Also in more chronic disease states, for example during severe pulmonary, cardiac, or renal failure, maintenance of life can be upheld by different artificial means until an organ for transplantation becomes available. In many clinical situations there is a need for an extracorporeal circuit wherein an artificial organ is incorporated.

Gas bubbles are easily formed in blood and are propelled into the circulation of a living being during extracorporeal circulation. Gas bubbles are formed from many sources, including cavitation, temperature gradients, and differences in the amount of gases dissolved between a subject's own and incoming blood, as well as inadvertent physical introduction of gas bubbles into blood by caregivers during surgical manipulation or parenteral administration of fluids. In the case of heart surgery, the extracorporeal circuit contains a gas-exchange device, for example an oxygenator, which is used for oxygenation and removal of carbon dioxide, for example. The close contact between blood and gas in the oxygenator poses significant risks for inadvertent entry of gas bubbles into the circulating blood.

At present, to avoid bubble formation during heart surgery, membrane-type oxygenators are used instead of bubble-oxygenators, high temperature gradients are avoided, and use of suction in the operating field is controlled. Heart-lung machines contain an air bubble sensor that warns the person controlling the heart-lung machine of the appearance of small bubbles, and immediately stops the main pump when larger bubbles appear. Typically, the bubble sensor can discern bubbles with a diameter of approximately 0.3 millimeters (mm) or larger, and stops the main pump when a bubble with a diameter of 3-5 mm is recognized.

Cardiac surgery is frequently complicated by postoperative neurocognitive deficits that degrade functional capacity and quality of life while increasing healthcare costs. Multifactorial contributors to this significant public health problem likely include gaseous microemboli (GME). The arterial circulation receives thousands of 10-40 micrometer ($\mu$m) diameter GME during cardiopulmonary bypass (CPB), despite the use of membrane oxygenation and arterial filtration. Vasooclusive GME cause tissue ischemia and denude endothelium in the brain and other end organs, leading to vascular dilation, increased permeability, activation of platelets and clotting cascades, and recruitment of complement and cellular mediators of inflammation.

Current perfusion practice targets mildly hyperoxic blood gases during CPB, by lowering the partial pressure of oxygen in oxygenator sweep gas by dilution with air, thereby producing the needless side effect of dissolving nitrogen in blood. The blood, thus saturated with dissolved gas, is poorly able to dissolve gases that exist in bubble form as GME.

Nonetheless, there remains a need to prevent or reduce the generation of gas bubbles, e.g., the formation of gas bubbles during heart surgery. In a blood bubble, in the liquid-gas interface, there is an approximately 40-100 Angstroms (Å) (4-10 nanometer) deep layer of lipoproteins that denaturate due to direct contact with the foreign material, e.g., gas. In turn, the Hageman factor is activated, which initiates coagulation and the concomitant adverse consumption of factors promoting coagulation, which are used to prevent bleeding from the surgical wound.

Accordingly, a system and method capable of inhibiting the bubble formation in the blood, as well as reducing the number and size of bubbles during extracorporeal circulation, is needed.

SUMMARY

Disclosed herein is a system and method for reducing gas bubbles, including gaseous microemboli (GME) during cardiopulmonary bypass (CPB). This approach reduces the number and size of GME, which can be useful in reducing postoperative complications, including neurocognitive deficits in CPB and other procedures. The system and method can be used for both in vitro and in vivo approaches. The system and method can be used in hypobaric and normobaric conditions.

A system for reducing gaseous microemboli, the system comprising a fluid source; a flow diverter fluidly connected to the fluid source, wherein the flow diverter is configured to remove a portion of the fluid from the fluid source; an inflow flow controller fluidly connected to the fluid source, wherein the inflow flow controller is configured to control the flow rate of fluid from the fluid source to the flow diverter; a bypass line fluidly connected to the flow diverter; a bypass flow controller fluidly connected to the bypass line, wherein the bypass flow controller is configured to control the flow rate of fluid from the bypass line; a filter in fluid communication with the bypass line, wherein the filter removes gaseous microemboli having a diameter greater than a stated pore size, preferably 15 to 50 micrometers; an oxygenator fluidly connected to the fluid source, wherein the oxygenator is configured to oxygenate the fluid from the fluid source; an outflow flow controller fluidly connected to the oxygenator, wherein the outflow flow controller is configured to control the flow rate of fluid from the oxygenator; an outlet fluidly connected to the oxygenator and the bypass line; a controller configured to control the inflow flow controller, the bypass flow controller, the outflow flow controller, or a combination comprising at least one or more of the foregoing, is provided.

A method for reducing gaseous microemboli, the method comprising providing an oxygenator configured to oxygenate a fluid, the oxygenator having a venous inlet, an arterial outlet, a venous bypass line fluidly connected to the venous inlet and the arterial outlet, wherein the venous bypass line comprises a filter configured to remove gaseous microemboli having a diameter greater than a stated pore size, preferably 15 to 50 micrometers, and wherein the venous bypass line is configured to remove a portion of the fluid from the venous inlet; introducing a fluid to the oxygenator; oxygenating the fluid passing through the oxygenator; combining the fluid from the venous bypass line and the arterial outlet, forming a combined fluid; wherein the partial pressure of dissolved oxygen in the combined fluid is 100 to 700 millimeters of mercury (mmHg), preferably 150 to 250 mmHg, is provided.

BRIEF DESCRIPTION OF THE FIGURES

The accompanying drawings incorporated in and forming a part of the specification embody several aspects of the present disclosure and, together with the description, serve to explain the principles of this disclosure. In the drawings.

DETAILED DESCRIPTION

Figure 1:
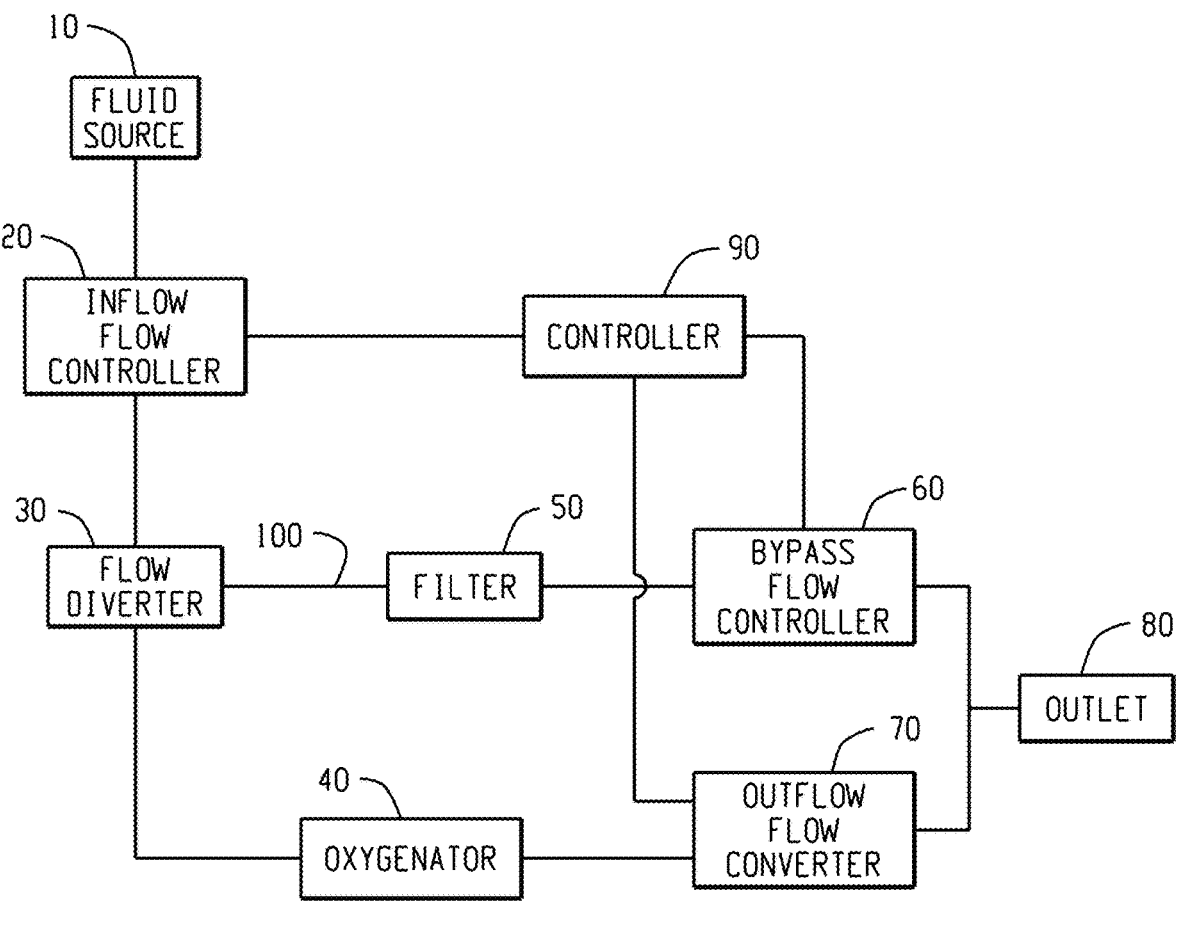
FIG. 1 is a schematic representation of an embodiment of a CPB system using a venous bypass with filter.

The following disclosure will detail particular exemplary embodiments, which provide methods and systems for reducing GME in a CPB system. An overview of the mechanism and methods used herein is provided.

The inventor hereof has unexpectedly solved the practical problem of shunting of GME around an oxygenator, by using an arterial filter in the shunt limb, in an embodiment.

This disclosure is directed to reduction of GME during CPB and other procedures including extracorporeal membrane oxygenation (ECMO), including veno-arterial ECMO and veno-venous ECMO, by the use of an oxygenator with venous blood bypass and a filter in the venous blood bypass. The systems and methods described can also be used for extracorporeal circulation systems including dialysis, continuous veno-venous hemofiltration (CVVH), and heart ventricular assist devices (VAD). Venous blood bypass takes a portion of the blood from the venous system or other source of non-oxygenated blood, bypasses the oxygenator, and introduces the bypassed venous blood into blood coming from the oxygenator. This mixture of oxygenated and non-oxygenated blood reduces the concentration of oxygen in the blood coming from the oxygenator, promoting removal of microbubbles from the blood. This approach allows the operation of the oxygenator using pure oxygen, nitrogen-free sweep gas, thereby avoiding both hyperoxemia that may be damaging to the patient and dissolved nitrogen that may oppose dissolution and removal of microbubbles

Although Applicant is not bound by any theory presented here, it is believed the mechanism for reducing GME described here involves reducing the sum of partial pressures of dissolved gases in the arterial blood returning to the patient, thereby permitting reabsorption of gases from bubbles into the blood phase.

In an embodiment, the gas profile in the mixed arterial blood traveling to the patient is around 150-250 mmHg dissolved oxygen (around 100 mmHg is the normal value in a healthy human) plus around 40 mmHg dissolved $CO_2$, for a sum of partial pressures of dissolved gases of 190-290 mmHg, which is hypobaric compared to the approximately 760 mmHg atmospheric pressure.

In an embodiment, all gas emboli, not matter how large or small, are removed in the filtered circuit. In an embodiment, emboli with diameter larger than a stated pore size of a filter, for example, between 15 to 50 micrometers, for example, greater than 15 micrometers, greater than 20 micrometers, greater than 28 micrometers, greater than 32 micrometers, greater than 37 micrometers, or greater than 40 micrometers, for example, are removed, and particles having a diameter less than the stated pore size pass through. In an embodiment, emboli having diameter larger than 50 micrometers, preferably larger than 40 micrometers, preferably larger than 28 micrometers are removed from the filtered circuit. Emboli in this size range are considered large enough to occlude capillaries but small enough to pass through an arterial filter.

As used herein, "fluid" and "blood" are used interchangeably, except as otherwise noted. It is to be understood that the systems and methods can be used for blood, or other fluids, such as a blood substitute, artificial blood, a blood product, such as plasma or albumin, platelets or plasma concentrates, crystalloids such as saline, lactated ringer's solution, normosol, plasmalyte, hetastarch, or other fluid, or a combination comprising at least one of the foregoing.

The fluid source can be from a subject, such as an animal, for example a human, or other mammal. The fluid source can be from a subject using cannulae inserted into the subject's venous or arterial system or heart chambers or body cavities, a fluid reservoir, or from a source outside a subject. The subject can be a patient undergoing treatment or evaluation.

The filter, because it acts as a resistance to flow, can be used to adjust or control flow in the bypass line.

A flow diverter is used to divert a portion of the blood and can be any suitable apparatus used to remove a portion of the fluid from the fluid source, such as a tubing tee, or a pump, or a separate non-gas-exchange shunt channel through an oxygenator.

The use of a separate non-gas-exchange shunt channel through an oxygenator can use 1) a filtered or non-filtered shunt channel within the oxygenator itself, the flow through which may or may not be regulatable or user-determined; or 2) a means of flowing sweep gas selectively to only a fraction of the sweep gas microtubules in the oxygenator fiber bundle, thereby allowing non-gas-exchange shunting to occur within the oxygenator without defeating the oxygenator's filtration role, for example. 2a) This approach can use a variable flap or device comprised of rubber, gel, polymer, foam, wax, plastic, metal, or other suitable material or reversible occlusion device to prevent gas flow through a portion of the fiber bundle near the sweep gas inlet or within the sweep gas inlet manifold, near the sweep gas outlet or within the sweep gas outlet manifold, or both, or anywhere along the sweep gas flow path. There can be more than one occlusion device used in a device, and a user or controller may be able to engage them in a desired combination to produce the desired amount of non-gas-exchange shunting. The occlusion may also be performed using a fluid or other suitable substance instilled into the sweep gas inlet manifold, or sweep gas outlet manifold, or both, for example water, oil, polymer, foam, or wax. 2b) This approach may also use a fluid or other suitable substance such as water, saline, crystalloid, colloid, blood product, oil, gel, polymer, foam, or wax instilled permanently or reversibly into the sweep gas inlet manifold or the sealed or unsealed sweep gas outlet manifold, or both, in order to prevent flow through a fraction of the sweep gas microtubules of the fiber bundle. Extra ports in dependent or non-dependent portions of the sweep gas inlet manifold or the sweep gas outlet manifold, or both, may be required to allow instillation and removal of substances to regulate sweep gas flow in the fiber bundle. Positive pressure relief valves in the sweep gas inlet manifold or the sweep gas outlet manifold, or both, may be required to relieve positive pressures that may result from limitation of sweep gas flow to a fraction of the fiber bundle. 2c) A non-gas-exchange shunt channel through an oxygenator can also be performed by dividing the oxygenator into compartments or using multiple oxygenators, where each compartment or oxygenator receives blood flow but the user can decide whether and how much sweep gas to flow in some of the compartments or oxygenators to achieve the desired level of non-gas-exchange shunting.

3) In the case of an oxygenator employing multiple compartments or during the use of multiple oxygenators, the same desirable effects on dissolved gases in blood and GME removal may be achieved in the absence of non-gas exchange shunting by directing blood and sweep gas flow to a minimum number of compartments or oxygenators necessary to achieve a user-defined oxygenation target but no more. The amount and flow characteristics of the fluid coming from the fluid source, such as flow velocity, flow volume, or other characteristic into the flow diverter can be controlled by an inflow controller, such as a needle valve, a mass flow controller, pump, or partial occlusion clamp. The inflow controller can be controlled independently, or can be controlled by a controller configured to control other aspects of the system, as described further herein.

The bypass line can be any suitable material, such as medical grade tubing, or other materials known to one of ordinary skill in the art without undue experimentation. The diameter, length, and composition of the bypass line is easily determined by one of ordinary skill in the art without undue experimentation.

The flow of fluid in the bypass line can be further controlled, for example to achieve the desired characteristics of fluid in the outlet. A sensor can be used in any desirable or useful location in the system to determine the actual or approximate number and size of GME or other particles, concentration of anticoagulants, anesthesia, or other medication, concentration of gases, such as oxygen, nitrogen, carbon dioxide, oxygen saturation of blood hemoglobin, or flow rate, for example. Flow rate and oxygen saturation sensors are applied external to the tubing and are standard. Blood samples are removed frequently, and in some cases continuously, for more detailed blood gas and anticoagulant analysis. The composition or other characteristics of the fluid in the bypass line can be altered from the composition or other characteristics of the fluid in the fluid source. For example, medication, such as anticoagulants or other medication, or gases, such as oxygen, nitrogen, carbon dioxide, or air, for example, can be added or removed to achieve the desired level of gases and other components.

In embodiments, a sensor is introduced at a location in the bypass line before the filter, a location in the bypass line after the filter, or a combination comprising one or more of the foregoing, to achieve the desired level of oxygen and other substances in the fluid in the bypass line.

A filter is inserted in the bypass line. The filter can be a so-called "arterial filter", as known in the art, designed to remove bubbles (GME), lipids, and other debris having a diameter greater than a stated pore size, for example, greater than 15 micrometers, greater than 20 micrometers, greater than 28 micrometers, greater than 32 micrometers, greater than 37 micrometers, or greater than 40 micrometers, for example, and let particles having a diameter less than the stated pore size pass through.

The filter pore size should be small enough to remove bubbles, but not so small as to prevent desired blood flows at reasonable pressures, known to one of ordinary skill in the art, or cause damage or filtering of cellular elements. The filter can also be a hemoconcentrator, bubble trap, or oxygenator, any of which may be operated under vacuum. The filter can be made from any suitable material, such as polyester.

The oxygenator can be any of a number of devices, such as a membrane oxygenator, a diffusion membrane oxygenator, or a hollow fiber microporous membrane oxygenator. In an embodiment, the oxygenator is a microporous membrane oxygenator with or preferably without a sealed housing. In an embodiment, the oxygenator is a microporous membrane oxygenator without a sealed housing. The connections of the fluid to and from the oxygenator, to and from the bypass line, and other connections are those known by one of ordinary skill in the art without undue experimentation. The operation of the oxygenator is known by one of ordinary skill in the art without undue experimentation.

The flow rate and volume, as well as other desired characteristics, of a fluid at any point in the system can be controlled by a flow controller, or other suitable device. A flow controller can be a needle valve, a mass flow controller, a pump, a clamp, or a partial occlusion clamp.

An outlet is fluidly connected to the oxygenator and the bypass line. The outlet can be the point where the fluid from the bypass line and the oxygenator are combined. A sensor can be used to measure a desired characteristic of the fluid at the outlet, for example, the concentration of anticoagulants or other medication, concentration of gases, such as oxygen, nitrogen, carbon dioxide, air, or blood oxygen saturation.

After the fluid is passed through the oxygenator and combined with the fluid from the venous bypass, the fluid can be stored, or reinfused into a subject or patient, for example.

Parameters of the system can be controlled by a controller, configured to control the inflow flow controller, the bypass flow controller, the outflow flow controller, or a combination comprising at least one or more of the foregoing. Each of the parameters of the system can also be controlled independently, such as by use of a manual valve.

In an embodiment, 0 to 50 percent of the total volume of the blood coming from the patient into the CPB system is diverted to the venous bypass. In an embodiment, 0 to 40 percent of the total volume of the blood coming from the patient into the CPB system is diverted to the venous bypass. In an embodiment, 0 to 30 percent of the total volume of the blood coming from the patient into the CPB system is diverted to the venous bypass. In an embodiment, 0 to 20 percent of the total volume of the blood coming from the patient into the CPB system is diverted to the venous bypass.

In an embodiment, 0 to 10 percent of the total volume of the blood coming from the patient into the CPB system is diverted to the venous bypass. In an embodiment, 0 to 5 percent of the total volume of the blood coming from the patient into the CPB system is diverted to the venous bypass. The blood entering the venous bypass can be filtered, cooled, warmed, fortified with various medications or gases, or otherwise treated. In an embodiment, the partial pressure of oxygen at the outlet is 50 to 800 mmHg. In an embodiment, the partial pressure of oxygen at the outlet is 100 to 700 mmHg. In an embodiment, the partial pressure of oxygen at the outlet is 75 to 650 mmHg. In an embodiment, the partial pressure of nitrogen at the outlet is zero. In an embodiment, the partial pressure of nitrogen at the outlet is minimized. In an embodiment, the partial pressure of nitrogen at the outlet is a nonzero level up to about 600 mmHg.

The desired parameters/composition of blood or fluid at the outlet (the point of mixing between blood from the oxygenator and blood from the shunt) depends on the goals of the surgical team and perfusionist for the patient. Frequently, the perfusionist will target an oxygen tension of 150-250 mmHg, a $CO_2$ tension of 40 mmHg, and an overall flow rate that is reasonably close to the patient's predicted normal cardiac output and which generates an adequate blood pressure in the patient's vascular system. In a common scenario, the perfusionist may flow 5 L/min of total flow, comprised of 1.5 L/min of flow through the shunt limb and 3.5 L/min of flow through the oxygenator. He or she may raise or lower the shunt fraction to adjust the $pO_2$, raise or lower the sweep gas flow rate to adjust the $pCO_2$, or raise or lower the flow rate to adjust the blood pressure.

In an embodiment, the filter acts to remove gaseous microemboli, as well as acts as a flow restrictor for the venous blood bypass, which can be used to control the oxygen level of the blood going back to the patient, for example. The method can be used in both normal baric and hypobaric conditions. In an embodiment, the oxygenator is configured to have a subatmospheric pressure, and can have a pressure of 0.4 to 1 atmospheres absolute. The described shunt can be used together with operating an oxygenator at subatmospheric pressure. In an embodiment, the system includes a vacuum regulator fluidly connected to the oxygenator, and configured to provide the subatmospheric pressure. In an embodiment, the oxygenator is configured to have atmospheric pressure.

The system can include one or more sensors configured to measure one or more of flow rate, fluid composition, oxygen saturation, carbon dioxide content, nitrogen content, temperature, hematocrit, or a combination comprising one or more of the foregoing, wherein the sensor is fluidly connected to the fluid source, the bypass line, the outlet, or a combination comprising one or more of the foregoing. These sensors can be any of a number of common sensors, known to one of ordinary skill in the art.

In an embodiment, the controller comprises a processor and software instructions implemented by the processor.

The fluid source can be a blender configured to combine one or more fluids.

The system can be used for a number of different fluids, such as blood, a blood substitute, artificial blood, a blood product, such as plasma or albumin, platelets or plasma concentrates, crystalloids such as saline, lactated ringer's solution, normosol, plasmalyte, hetastarch, or other fluid, or a combination comprising one or more of the foregoing.

Also provided is a method for reducing gaseous microemboli, the method including providing an oxygenator configured to oxygenate a fluid, the oxygenator having a venous inlet, an arterial outlet; a venous bypass line fluidly connected to the venous inlet and the arterial outlet, wherein the venous bypass line comprises a filter configured to remove gaseous microemboli greater than a stated pore size, typically 15 to 50 micrometers, or 28 to 40 micrometers, for example, and wherein the venous bypass line is configured to remove a portion of the fluid from the venous inlet; introducing a fluid to the oxygenator; oxygenating the fluid passing through the oxygenator, typically using pure oxygen sweep gas; combining the fluid from the venous bypass line and the arterial outlet, forming a combined fluid; wherein the concentration of oxygen in the combined fluid is 75 to 800 mmHg, preferably 100 to 700 mmHg, preferably 100 to 650 mmHg, preferably 150 to 250 mmHg. The oxygenator can be any suitable apparatus that can introduce oxygen to a fluid and remove carbon dioxide from a fluid. The method can further include introducing medication or gases into the fluid. The method can further include measuring the concentration of oxygen, nitrogen, carbon dioxide, anesthesia, medication, oxygen saturation, or other substances at any point including the blood and the gas at the sweep gas outlet. The measuring can be performed using any suitable measurement apparatus or sampling technique, such as the use of an inline dual-wavelength oximeter, or the use of a sampling technique where a portion of the fluid is removed for analysis. The method can further include monitoring or controlling the temperature of the fluid at any point.

The system and method can also include a non-gas-exchange shunt channel through the oxygenator, instead of, or in addition to the shunt limb. In an embodiment, one of a non-gas-exchange shunt channel through the oxygenator or the shunt limb is used. In an embodiment, a non-gas-exchange shunt channel through the oxygenator is used. The non-gas-exchange shunt channel can be a filtered shunt flow channel within the oxygenator, wherein the flow rate through the filtered shunt flow channel is optionally regulatable. In an embodiment, the oxygenator can be fluidly connected to a sweep gas reservoir or source via a sweep gas inlet and a sweep gas outlet, wherein the oxygenator comprises sweep gas microtubules in a fiber bundle, and the non-gas-exchange shunt channel comprises a means of flowing sweep gas selectively to a fraction of the sweep gas microtubules in the oxygenator fiber bundle, wherein non-gas-exchange shunting occurs within the oxygenator. In an embodiment, the oxygenator is fluidly connected to a sweep gas reservoir via a sweep gas inlet and a sweep gas outlet, and the means of flowing sweep gas selectively to a fraction of the sweep gas microtubules in the oxygenator fiber bundle comprises a variable flow flap or occlusion device, wherein the variable flow flap or occlusion device prevents gas flow through a portion of the fiber bundle near the sweep gas inlet, near the sweep gas outlet, or both, or anywhere along the flow path of the fluid from the fluid source. In an embodiment, the oxygenator comprises two or more compartments, wherein the flow of sweep gas in each compartment is independently adjustable. In the embodiment where the system comprises more than one oxygenator, each oxygenator can be fluidly connected to a sweep gas reservoir via a sweep gas inlet and a sweep gas outlet, and each oxygenator can receive fluid from the fluid source, and the flow of sweep gas to each oxygenator is independently adjustable. In an embodiment where the oxygenator comprises two or more compartments, blood flow to each compartment is independently adjustable so that blood flow may be withheld from some compartments to use only as much oxygenating capacity as necessary to achieve the target level of dissolved oxygen and no more. In an embodiment where multiple oxygenators are used, blood flow to each oxygenator is independently adjustable so that blood flow may be withheld from some oxygenators to use only as much oxygenating capacity as necessary to achieve the target level of dissolved oxygen and no more. In an embodiment, the partial pressure of nitrogen at the outlet is reduced or minimized compared with standard oxygenation strategies incorporating air.

The system and method can be used with any CPB system or circuit, including the system described in WO2015/047927, for example, which is hereby incorporated by reference in its entirety.

EXAMPLES

The following examples are non-limiting. Reference is now made to the drawings, wherein like reference numerals are used to refer to like elements throughout the disclosure.

FIG. 1 shows a schematic of an exemplary embodiment of a system using venous bypass with a filter to reduce GME. Fluid (which can be gas, liquid, dissolved gas, or a combination comprising one or more of the foregoing) from fluid source 10 passes into optional inflow flow controller 20 which controls the flow rate, amount, and other characteristics of fluid from fluid source 10 into flow diverter 30. Optional inflow flow controller 20 can be a pump in a CPB circuit. The bypass and outflow flow controllers, elements 60 and 70, are also optional. Optional controller 90 can control inflow flow controller 20, bypass flow controller 60 and/or outflow flow controller 70. Flow diverter 30 can be any of a number of suitable embodiments, such as a tee for diverting a fluid stream into two or more paths, a valve, or other suitable device. Fluid from flow diverter 30 passes into oxygenator 40 and bypass line 100. The percentage of fluid from fluid source 10 that passes into oxygenator 40 and bypass line 100 can vary, depending on a number of factors, including the amount of a desired substance such as oxygen, or other substance in outlet 80, the desired fluid volume at outlet 80, or other factors. Oxygenator 40 can be any of a number of apparatus or systems useful for adding oxygen to a fluid and removing carbon dioxide. Bypass line 100 includes filter 50. Filter 50 can be a so-called "arterial filter", typically used in CPB to reduce the number and size of GME. Filter 50 can be a screen filter where a filter medium having a desired pore size, as described elsewhere herein, is used to remove particles larger than the pore size of the filter medium. Filter 50 can be a depth filter, where a filter has a thickness where larger particles are trapped in the surface layers, while smaller particles are trapped by succeeding layers. The desired pore size or filter thickness can be varied, to remove or reduce the number of particles having a selected size. As an example, a screen filter can be used where the filter medium has a pore size of 50 micrometers, 40 micrometers, 25 micrometers, 15 micrometers, or other size that removes GME, but does not filter white blood cells or other desired blood constituents, or does not restrict the flow so that the needed or desired flow rate cannot be achieved. In an embodiment, the filter accommodates adequate flow rates. The volume, flow rate, or other parameters of fluid from filter 50 can be controlled by bypass flow controller 60. The volume, flow rate, or other parameters of fluid from oxygenator 40 can be controlled by outflow flow controller 70. Fluid from bypass line 100 and oxygenator 40 are combined at outlet 80.

Parameters of the fluid, such as concentration of oxygen, nitrogen, carbon dioxide, anesthesia, medication, or other substance can be measured and adjusted at any point, as described herein.

Figure 2:
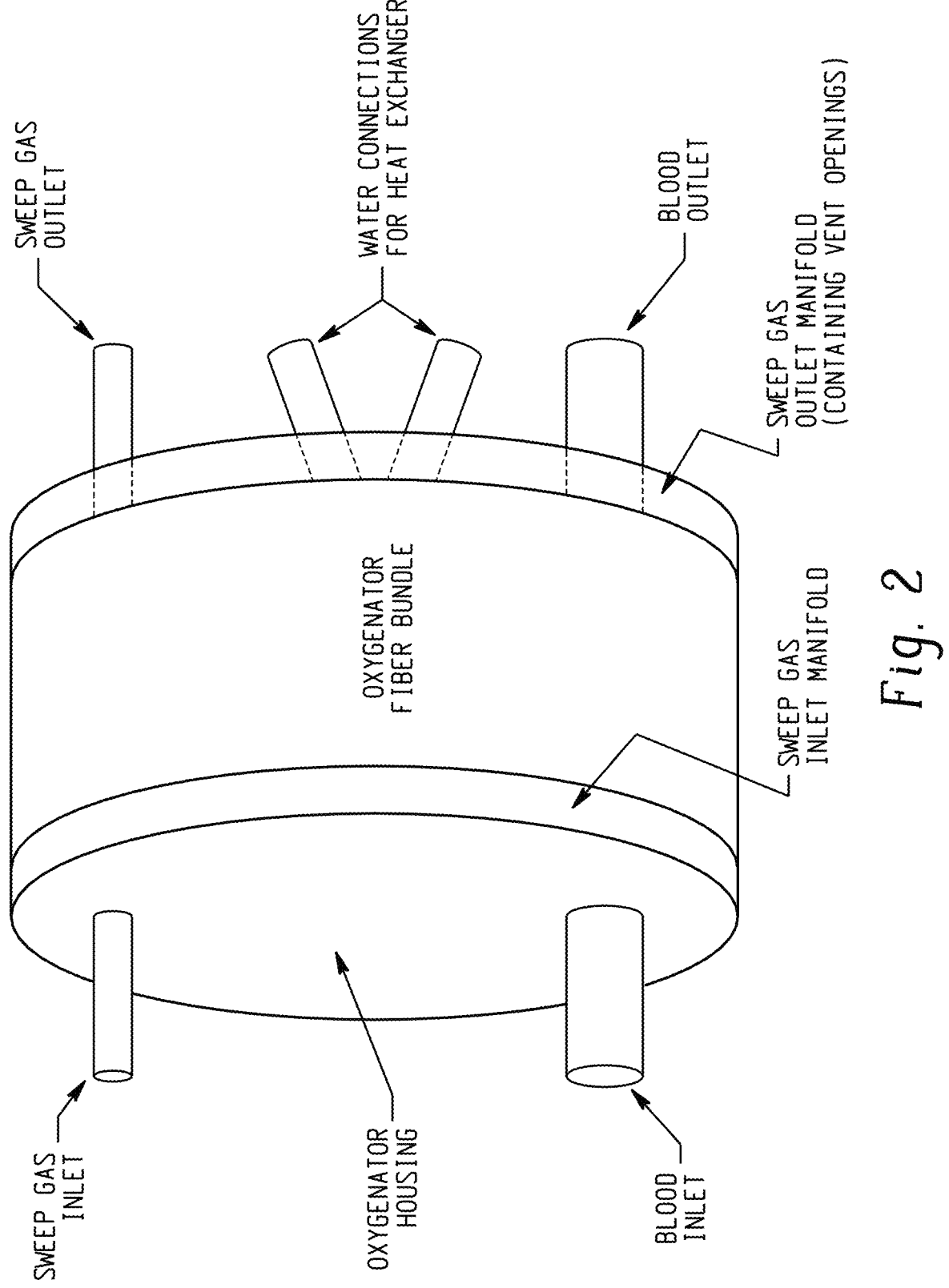
FIG. 2 is a schematic representation of an oxygenator that can be used.

FIG. 2 illustrates an exemplary oxygenator that can be used. In FIG. 2, the oxygenator is shown with a housing, a blood inlet and blood outlet, a sweep gas inlet and outlet, and a sweep gas inlet manifold and sweep gas outlet manifold (containing vent openings). The oxygenator is shown having a fiber bundle. Water connectors for heat exchange are also shown. The oxygenator can use any suitable membrane, such as polypropylene. Gas vents can be used to control the pressure of the oxygenator.

Figures 3, 4:
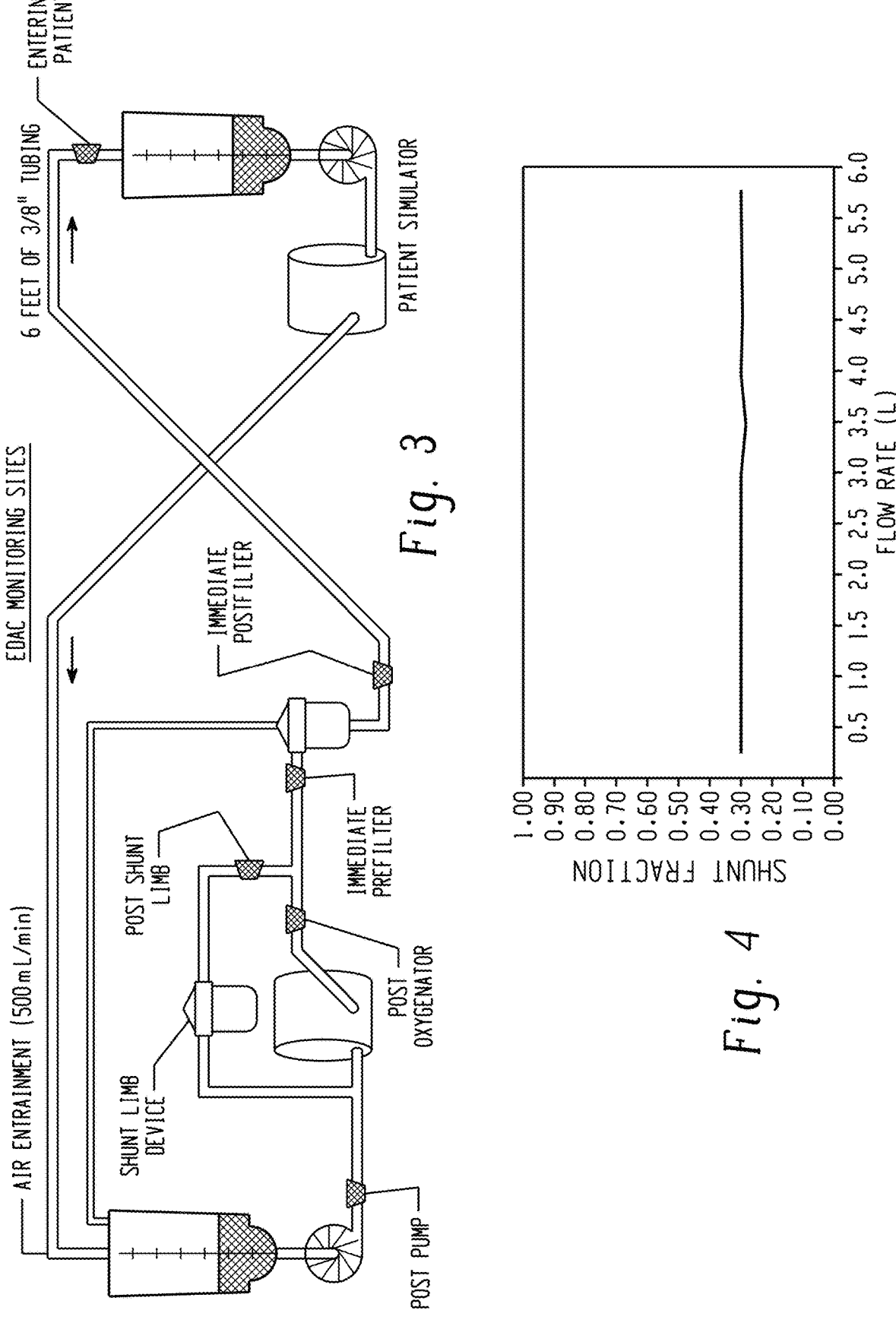
FIG. 3 shows a heart-lung machine circuit used to obtain the data provided here.
FIG. 4 shows experimental data showing the fraction of total flow traveling through the shunt limb over a large range of total flow rates.

FIG. 3 shows a heart-lung machine circuit used for the data provided here.

In FIG. 3, a CPB bypass circuit with Emboli Detection and Classification (EDAC) and venous air entrainment sites (500 mL/minute) is shown.

FIG. 4 shows experimental data showing that addition of a filter (Terumo AF125x) to the shunt limb ("shunt limb device" in FIG. 3, for example) effectively limits the shunt fraction to a safe level, and that this level is stable over a wide range of CPB flow rates.

Figure 5:
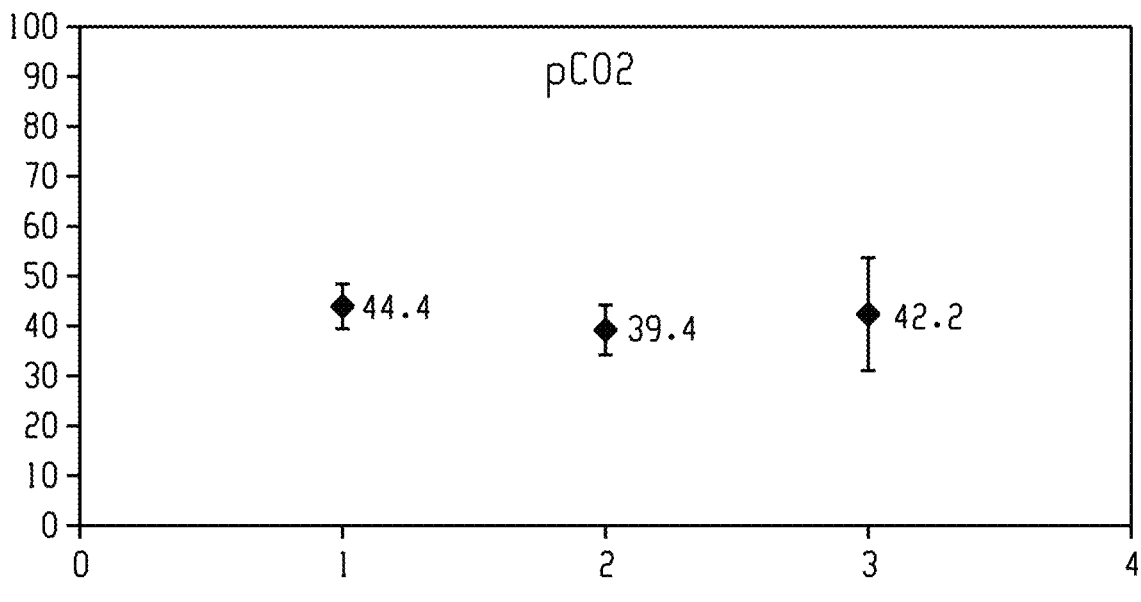
FIG. 5 shows experimental data showing the partial pressure of dissolved $CO_2$ or $O_2$ under three different conditions.
Figure 5:
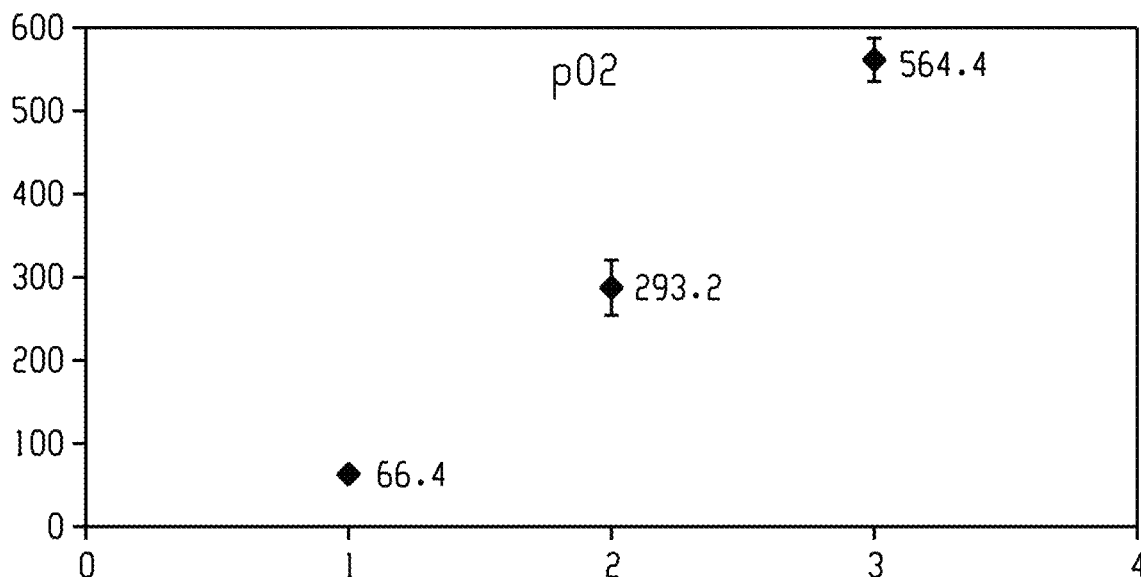

FIG. 5 provides experimental data showing that a filtered shunt in the heart-lung machine reduces dissolved $O_2$ in arterial blood to a safe, mildly hyperoxic, level like that targeted by perfusionists during CPB. The sweep gases were free of nitrogen, so the demonstrated levels of dissolved $O_2$ and $CO_2$ represent the only dissolved gases in the blood. FIG. 5 provides data for three conditions, measurement of the $pCO_2$ and $pO_2$ in venous blood from the patient simulator (Condition 1); measurement of the $pCO_2$ and $pO_2$ in arterial blood from the heart-lung machine with the filtered shunt in place (Condition 2); and measurement of the $pCO_2$ and $pO_2$ in arterial blood from the heart-lung machine with no shunt (Condition 3). In FIG. 5, the Y-axes are partial pressures of dissolved $CO_2$ or $O_2$ in mmHg. In FIG. 5, the X-axes are the conditions described above.

Figure 6:
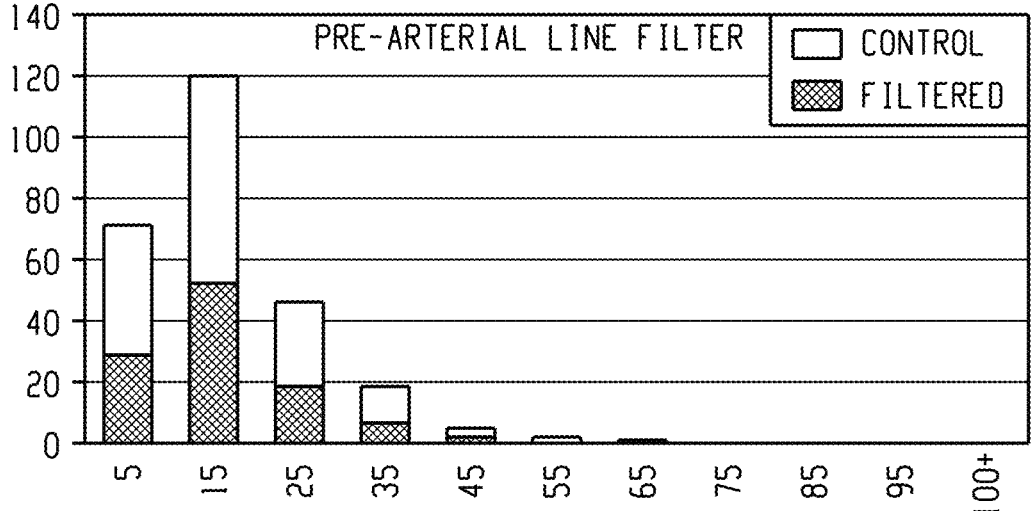
FIG. 6 shows experimental data showing reduction of GME at two locations in a CPB system.
Figure 6:
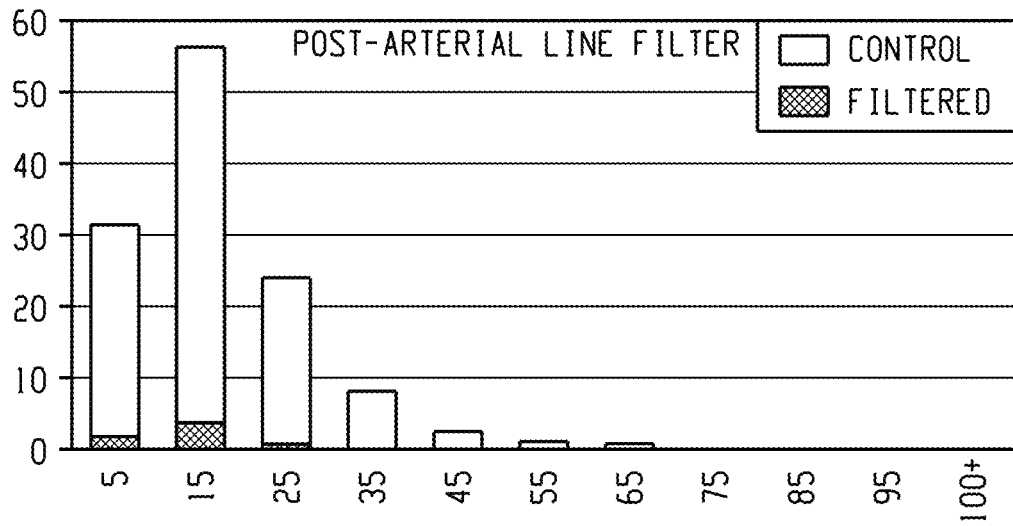

FIG. 6 provides experimental data showing reduction of GME before (upper graph titled "Pre Arterial Line Filter") and after the arterial line filter (lower graph titled "Post Arterial Line Filter") when using a filtered shunt compared to control (no shunt). The reduction of GME after the arterial line filter is measured downstream of the oxygenator/filtered shunt in question and on the way to the patient. In FIG. 6, control=no shunt; filtered=filtered shunt; y-axes are emboli per minute; and x-axes are emboli diameter in micrometers.

Figure 7:
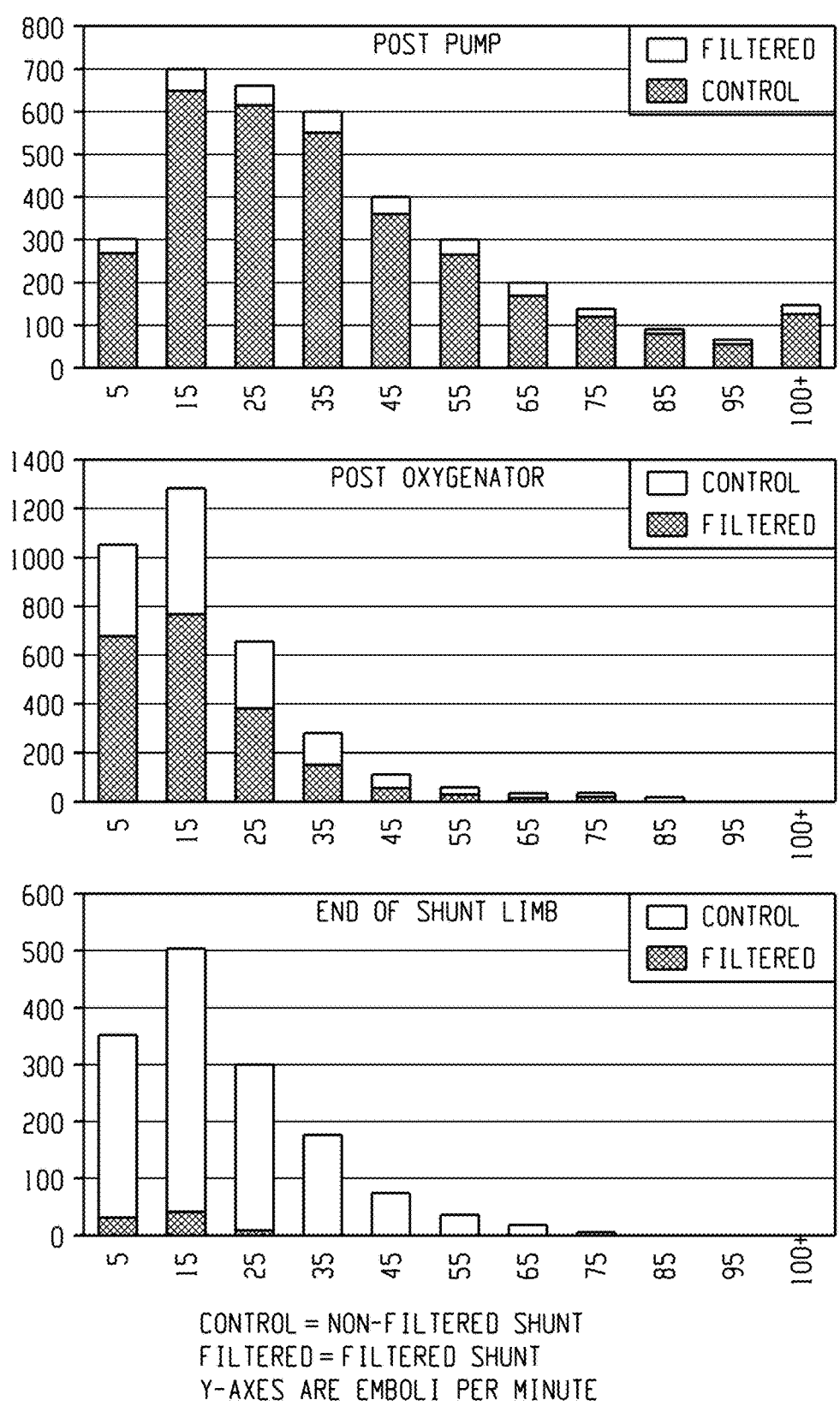
FIG. 7 shows experimental data showing reduction of GME delivery through the shunt limb in the presence of an arterial filter at three locations in the CPB bypass circuit.

FIG. 7 provides experimental data showing GME at three locations in the CPB bypass circuit: post pump, post oxygenator, and at the end of the shunt limb (referred to as "Post Shunt Limb" in FIG. 3). In FIG. 7, control=non-filtered shunt; filtered=filtered shunt; y-axes represent emboli per minute; and x-axes represent emboli diameter.

Figure 8:
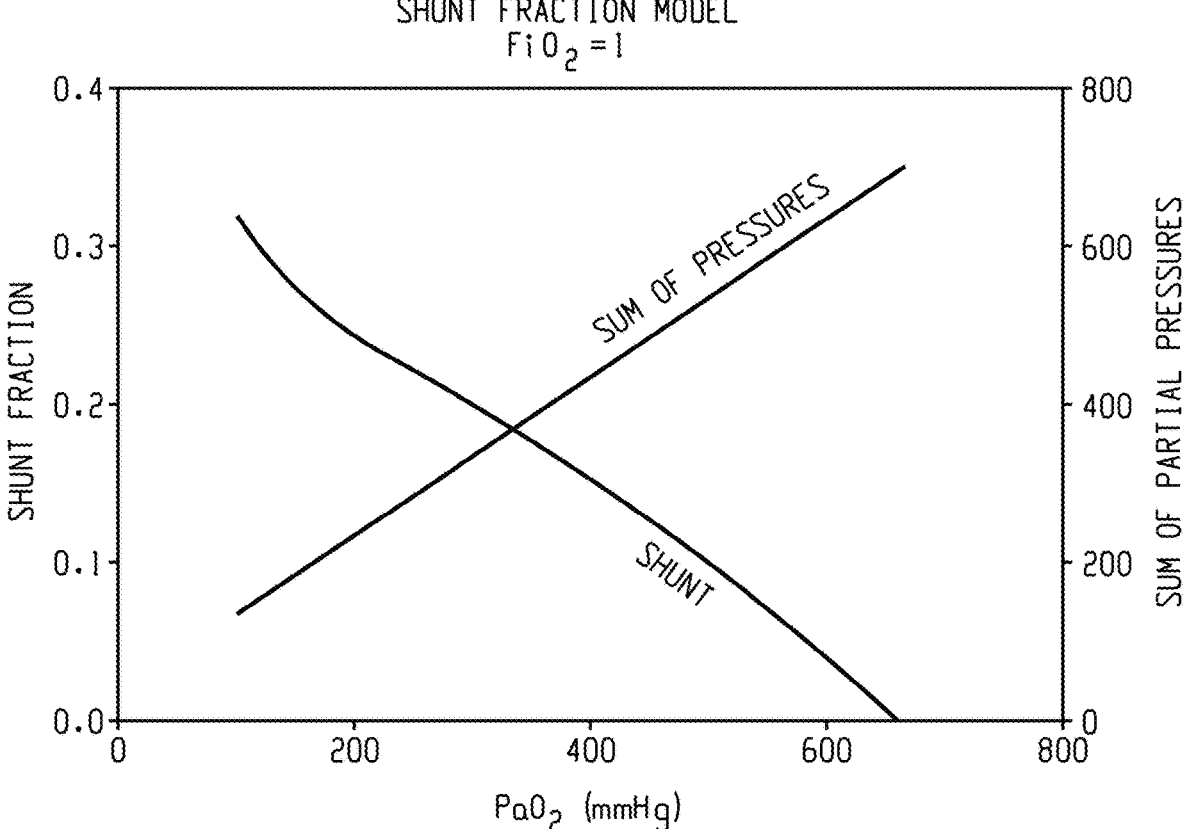
FIG. 8 shows the sum of the partial pressures as a function of the shunt fraction.

FIG. 8 shows a mathematical model of the sum of the partial pressures as a function of the shunt fraction.

The addition of a filter to the shunt limb reduces shunting of GME through the shunt limb, which is useful to the GME reduction strategy provided.

EMBODIMENTS

The methods and systems are further illustrated by the following embodiments, which are non-limiting.

Embodiment 1: a system for reducing gaseous microemboli, the system comprising a fluid source; a flow diverter fluidly connected to the fluid source, wherein the flow diverter is configured to remove a portion of the fluid from the fluid source; an inflow flow controller fluidly connected to the fluid source, wherein the inflow flow controller is configured to control the flow rate of fluid from the fluid source to the flow diverter; a bypass line fluidly connected to the flow diverter; a bypass flow controller fluidly connected to the bypass line, wherein the bypass flow controller is configured to control the flow rate of fluid from the bypass line; a filter in fluid communication with the bypass line, wherein the filter removes gaseous microemboli having a diameter greater than a stated pore size, preferably 15 to 50 micrometers; an oxygenator fluidly connected to the fluid source, wherein the oxygenator is configured to oxygenate the fluid from the fluid source; an outflow flow controller fluidly connected to the oxygenator, wherein the outflow flow controller is configured to control the flow rate of fluid from the oxygenator; an outlet fluidly connected to the oxygenator and the bypass line; a controller configured to control the inflow flow controller, the bypass flow controller, the outflow flow controller, or a combination comprising at least one or more of the foregoing.

Embodiment 2: The system of Embodiment 1, wherein the oxygenator is configured to have a subatmospheric pressure.

Embodiment 3: The system of any of Embodiment 1 to 2, further comprising a vacuum regulator fluidly connected to the oxygenator, and configured to provide the subatmospheric pressure.

Embodiment 4: The system of any of Embodiments 1 to 3, wherein the oxygenator is configured to have atmospheric pressure.

Embodiment 5: The system of any of Embodiment 1 to 4, further comprising a sensor configured to measure one or more of flow rate, fluid composition, blood oxygen saturation, oxygen tension, carbon tension fraction, nitrogen tension, hematocrit, or a combination comprising one or more of the foregoing, wherein the sensor is fluidly connected to the fluid source, the bypass line, the outlet, or a combination comprising one or more of the foregoing.

Embodiment 6: The system of any of Embodiment 1 to 5, wherein the controller comprises a processor and software instructions implemented by the processor.

Embodiment 7: The system of any of Embodiment 1 to 6, wherein the oxygenator is a membrane oxygenator, a diffusion membrane oxygenator, or a hollow fiber microporous membrane oxygenator.

Embodiment 8: The system of Embodiment 7, wherein the oxygenator is a microporous membrane oxygenator with a sealed housing.

Embodiment 9: The system of any of Embodiment 1 to 8, wherein the fluid is blood, a blood substitute, artificial blood, a blood product, such as plasma or albumin, platelets or plasma concentrates, crystalloids such as saline, lactated ringer's solution, normosol, plasmalyte, hetastarch, or a combination comprising at least one of the foregoing.

Embodiment 10: The system of any of Embodiment 1 to 9, wherein the fluid source is a blender configured to combine one or more fluids.

Embodiment 11: The system of any of Embodiment 1 to 10, wherein a blood flows within the system.

Embodiment 12: The system of any of Embodiment 1 to 11, wherein the concentration of oxygen at the outlet is 75 to 800 mmHg, preferably 100 to 700 mmHg, preferably 100 to 650 mmHg, preferably 150 to 250 mmHg.

Embodiment 13: The system of any of Embodiment 1 to 12, wherein the partial pressure of nitrogen at the outlet is reduced or minimized compared with standard oxygenation strategies incorporating air.

Embodiment 14: A method for reducing gaseous microemboli, the method comprising providing an oxygenator configured to oxygenate a fluid, the oxygenator having a venous inlet, an arterial outlet; a venous bypass line fluidly connected to the venous inlet and the arterial outlet, wherein the venous bypass line comprises a filter configured to remove gaseous microemboli having a diameter greater than a stated pore size, preferably 15-50 micrometers, and wherein the venous bypass line is configured to remove a portion of the fluid from the venous inlet; introducing a fluid to the oxygenator; oxygenating the fluid passing through the oxygenator; combining the fluid from the venous bypass line and the arterial outlet, forming a combined fluid; wherein the concentration of oxygen in the combined fluid is 100 to 700 mmHg, preferably 150 to 250 mmHg.

Embodiment 15: The method of Embodiment 14, comprising shunting a portion of the flow through a non-gas-exchange shunt channel is a filtered shunt flow channel within the oxygenator.

Embodiment 16: The method of any of Embodiment 14 to 15, wherein the flow rate through the filtered shunt flow channel is optionally regulatable.

Embodiment 17: The method of any of Embodiment 14 to 16, further comprising limiting the fluid flow passing through the oxygenator.

Embodiment 18: The system of any of Embodiment 1 to 13, further comprising a non-gas-exchange shunt channel through the oxygenator.

Embodiment 19: The system of any of Embodiment 1 to 13 or 18, wherein the non-gas-exchange shunt channel is a filtered shunt flow channel within the oxygenator, wherein the flow rate through the filtered shunt flow channel is optionally regulatable.

Embodiment 20: The system of any of Embodiment 1 to 13 or 18 to 19, wherein the oxygenator is fluidly connected to a sweep gas reservoir or source via a sweep gas inlet and a sweep gas outlet, and wherein the oxygenator comprises sweep gas microtubules in a fiber bundle, and the non-gas-exchange shunt channel comprises a means of flowing sweep gas selectively to a fraction of the sweep gas microtubules in the oxygenator fiber bundle, wherein non-gas-exchange shunting occurs within the oxygenator.

Embodiment 21: The system of any of Embodiment 1 to 13 or 18 to 20, wherein the oxygenator is fluidly connected to a sweep gas reservoir via a sweep gas inlet and a sweep gas outlet, and the means of flowing sweep gas selectively to a fraction of the sweep gas microtubules in the oxygenator fiber bundle comprises a variable flow flap or occlusion device, wherein the variable flow flap or occlusion device prevents gas flow through a portion of the fiber bundle near the sweep gas inlet, near the sweep gas outlet, or both, or anywhere along the flow path of the fluid from the fluid source.

Embodiment 22: The system of any of Embodiment 1 to 13 or 18 to 21, wherein the oxygenator is fluidly connected to a sweep gas reservoir via a sweep gas inlet and a sweep gas outlet, and the means of flowing sweep gas selectively to a fraction of the sweep gas microtubules in the oxygenator fiber bundle comprises a fluid or other suitable substance such as water, saline, crystalloid, colloid, blood product, oil, gel, polymer, foam, or wax instilled permanently or reversibly into the sweep gas inlet manifold or the sealed or unsealed sweep gas outlet manifold, or both, in order to prevent flow through a fraction of the sweep gas microtubules of the fiber bundle.

Embodiment 22: The system of any of Embodiment 1 to 13 or 18 to 21, wherein the oxygenator housing contains extra ports in dependent or non-dependent portions of the sweep gas inlet manifold or the sweep gas outlet manifold, or both, to allow instillation and removal of substances to regulate sweep gas flow in the fiber bundle.

Embodiment 23: The system of any of Embodiment 1 to 13 or 18 to 22, wherein the oxygenator housing contains positive pressure relief valves in the sweep gas inlet manifold or the sweep gas outlet manifold, or both, to relieve positive pressures that may result from limitation of sweep gas flow to a fraction of the fiber bundle.

Embodiment 24: The system of any of Embodiment 1 to 13 or 18 to 23, wherein the oxygenator comprises two or more compartments, wherein the flow of sweep gas in each compartment is independently adjustable.

Embodiment 25: The system of any of Embodiment 1 to 13 or 18 to 24, wherein the oxygenator comprises two or more compartments, wherein the flow of blood in each compartment is independently adjustable.

Embodiment 26: The system of any of Embodiment 1 to 13 or 18 to 25, wherein the system comprises more than one oxygenator, wherein each oxygenator is fluidly connected to a sweep gas reservoir via a sweep gas inlet and a sweep gas outlet, wherein each oxygenator receives fluid from the fluid source, and wherein the flow of sweep gas to each oxygenator is independently adjustable.

Embodiment 27: The system any of Embodiment 1 to 13 or 18 to 26, wherein the system comprises more than one oxygenator, wherein each oxygenator is fluidly connected to a blood reservoir or source via a blood inlet and a blood outlet, wherein each oxygenator receives fluid from the fluid source, and wherein the flow of blood to each oxygenator is independently adjustable.

Embodiment 28: The system of any of Embodiment 1 to 13 or 18 to 27, wherein the partial pressure of nitrogen at the outlet is reduced or minimized compared with standard oxygenation strategies incorporating air.

Also disclosed is system for reducing gaseous microemboli, the system comprising a fluid source; a flow diverter fluidly connected to the fluid source, wherein the flow diverter is configured to remove a portion of the fluid from the fluid source; an inflow flow controller fluidly connected to the fluid source, wherein the inflow flow controller is configured to control the flow rate of fluid from the fluid source to the flow diverter; a bypass line fluidly connected to the flow diverter; a bypass flow controller fluidly connected to the bypass line, wherein the bypass flow controller is configured to control the flow rate of fluid from the bypass line; a filter in fluid communication with the bypass line, wherein the filter removes gaseous microemboli having a diameter greater than a stated pore size, preferably 15 to 50 micrometers; an oxygenator fluidly connected to the fluid source, wherein the oxygenator is configured to oxygenate the fluid from the fluid source; an outflow flow controller fluidly connected to the oxygenator, wherein the outflow flow controller is configured to control the flow rate of fluid from the oxygenator; an outlet fluidly connected to the oxygenator and the bypass line; a controller configured to control the inflow flow controller, the bypass flow controller, the outflow flow controller, or a combination comprising at least one or more of the foregoing.

Also disclosed is a method for reducing gaseous microemboli, the method comprising providing an oxygenator configured to oxygenate a fluid, the oxygenator having a venous inlet, an arterial outlet; a venous bypass line fluidly connected to the venous inlet and the arterial outlet, wherein the venous bypass line comprises a filter configured to remove gaseous microemboli having a diameter greater than a stated pore size, preferably 15 to 50 micrometers, and wherein the venous bypass line is configured to remove a portion of the fluid from the venous inlet; introducing a fluid to the oxygenator; oxygenating the fluid passing through the oxygenator; combining the fluid from the venous bypass line and the arterial outlet, forming a combined fluid; wherein the concentration of oxygen in the combined fluid is 100 to 700 mmHg, preferably 150 to 250 mmHg.

In any of the foregoing embodiments, the oxygenator is configured to have a subatmospheric pressure; and/or further comprising a vacuum regulator fluidly connected to the oxygenator, and configured to provide the subatmospheric pressure; and/or the oxygenator is configured to have atmospheric pressure; and/or further comprising a sensor configured to measure one or more of flow rate, fluid composition, blood oxygen saturation, oxygen tension, carbon tension fraction, nitrogen tension, hematocrit, or a combination comprising one or more of the foregoing, wherein the sensor is fluidly connected to the fluid source, the bypass line, the outlet, or a combination comprising one or more of the foregoing; and/or the controller comprises a processor and software instructions implemented by the processor; and/or the oxygenator is a membrane oxygenator, a diffusion membrane oxygenator, or a hollow fiber microporous membrane oxygenator; and/or the oxygenator is a microporous membrane oxygenator with a sealed housing; and/or the fluid is blood, a blood substitute, artificial blood, a blood product, such as plasma or albumin, platelets or plasma concentrates, crystalloids such as saline, lactated ringer's solution, normosol, plasmalyte, hetastarch, or a combination comprising at least one of the foregoing; and/or the fluid source is a blender configured to combine one or more fluids; and/or a blood flows within the system; and/or the concentration of oxygen at the outlet is 75 to 800 mmHg, preferably 100 to 700 mmHg, preferably 100 to 650 mmHg, preferably 150 to 250 mmHg; and/or further comprising a non-gas-exchange shunt channel through the oxygenator; and/or the non-gas-exchange shunt channel is a filtered shunt flow channel within the oxygenator, wherein the flow rate through the filtered shunt flow channel is optionally regulatable; and/or the oxygenator is fluidly connected to a sweep gas reservoir or source via a sweep gas inlet and a sweep gas outlet, and wherein the oxygenator comprises sweep gas microtubules in a fiber bundle, and the non-gas-exchange shunt channel comprises a means of flowing sweep gas selectively to a fraction of the sweep gas microtubules in the oxygenator fiber bundle, wherein non-gas-exchange shunting occurs within the oxygenator; and/or the oxygenator is fluidly connected to a sweep gas reservoir or source via a sweep gas inlet and a sweep gas outlet, and the means of flowing sweep gas selectively to a fraction of the sweep gas microtubules in the oxygenator fiber bundle comprises a variable flow flap or occlusion device, wherein the variable flow flap or occlusion device prevents gas flow through a portion of the fiber bundle near the sweep gas inlet, near the sweep gas outlet, or both, or anywhere along the flow path of the fluid from the fluid source; and/or the oxygenator is fluidly connected to a sweep gas reservoir or source via a sweep gas inlet and a sweep gas outlet, and the means of flowing sweep gas selectively to a fraction of the sweep gas microtubules in the oxygenator fiber bundle comprises a fluid or other suitable substance such as water, saline, crystalloid, colloid, blood product, oil, gel, polymer, foam, or wax instilled permanently or reversibly into the sweep gas inlet manifold or the sealed or unsealed sweep gas outlet manifold, or both, in order to prevent flow through a fraction of the sweep gas microtubules of the fiber bundle; and/or the oxygenator housing contains extra ports in dependent or non-dependent portions of the sweep gas inlet manifold or the sweep gas outlet manifold, or both, to allow instillation and removal of substances to regulate sweep gas flow in the fiber bundle; and/or the oxygenator housing contains positive pressure relief valves in the sweep gas inlet manifold or the sweep gas outlet manifold, or both, to relieve positive pressures that may result from limitation of sweep gas flow to a fraction of the fiber bundle; and/or the oxygenator comprises two or more compartments, wherein the flow of sweep gas in each compartment is independently adjustable; and/or the oxygenator comprises two or more compartments, wherein the flow of blood in each compartment is independently adjustable; and/or the system comprises more than one oxygenator, wherein each oxygenator is fluidly connected to a sweep gas reservoir via a sweep gas inlet and a sweep gas outlet, wherein each oxygenator receives fluid from the fluid source, and wherein the flow of sweep gas to each oxygenator is independently adjustable; and/or the system comprises more than one oxygenator, wherein each oxygenator is fluidly connected to a blood reservoir or source via a blood inlet and a blood outlet, wherein each oxygenator receives fluid from the fluid source, and wherein the flow of blood to each oxygenator is independently adjustable; and/or wherein the partial pressure of nitrogen at the outlet is reduced or minimized compared with standard oxygenation strategies incorporating air; and/or further comprising shunting a portion of the flow through a non-gas-exchange shunt channel which is a filtered shunt flow channel within the oxygenator; and/or the flow rate through the filtered shunt flow channel is optionally regulatable; and/or limiting the fluid flow passing through the oxygenator.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Exemplary embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A system for reducing gaseous microemboli, the system comprising
    a blood source; and
    an oxygenator configured to oxygenate blood from the blood source,
        wherein the oxygenator comprises two or more compartments configured to allow independent adjustment of a sweep gas in each compartment, a flow of blood in each compartment, or a combination thereof.

2. The system of claim 1, wherein the oxygenator is a membrane oxygenator.

3. The system of claim 1, wherein the oxygenator is a hollow fiber microporous membrane oxygenator.

4. The system of claim 1, wherein the oxygenator is a microporous membrane oxygenator with a sealed housing.

5. The system of claim 1, wherein the oxygenator comprises sweep gas microtubules in a fiber bundle.

6. The system of claim 1, wherein the two or more compartments are configured to allow independent adjustment of the sweep gas in each compartment.

7. The system of claim 6, wherein the two or more compartments are configured to allow independent adjustment of a flow of the sweep gas in each compartment.

8. The system of claim 1, wherein the blood source comprises a blood reservoir.

9. A method for reducing gaseous microemboli using the system of claim 1, the method comprising
    oxygenating the blood in the oxygenator, and
    independently adjusting the sweep gas in each compartment, the flow of blood in each compartment, or the combination thereof.

10. The method of claim 9, comprising independently adjusting the sweep gas in each compartment.

11. The method of claim 10, comprising independently adjusting a flow of the sweep gas in each compartment.

12. A system for reducing gaseous microemboli, the system comprising
    a blood source; and
    more than one oxygenator configured to oxygenate blood from the blood source,
    wherein
        each oxygenator is fluidly connected to a sweep gas source via a sweep gas inlet, and wherein the oxygenators are configured to allow independent adjustment of a sweep gas to each oxygenator, or
        each oxygenator is fluidly connected to a blood source via a blood inlet, and wherein the oxygenators are configured to allow independent adjustment of a flow of blood to each oxygenator.

13. The system of claim 12, wherein each oxygenator is fluidly connected to the sweep gas source via the sweep gas inlet, and wherein the oxygenators are configured to allow independent adjustment of the sweep gas to each oxygenator.

14. The system of claim 13, wherein the oxygenators are configured to allow independent adjustment of a flow of the sweep gas to each oxygenator.

15. The system of claim 12, wherein the sweep gas source comprises a sweep gas reservoir.

16. A method for reducing gaseous microemboli using the system of claim 12, the method comprising oxygenating the blood in the oxygenator, and independently adjusting the sweep gas to each oxygenator, the flow of blood to each oxygenator, or a combination thereof.

17. A system for reducing gaseous microemboli, the system comprising a blood source;

an oxygenator configured to oxygenate blood from the blood source; and means of flowing a sweep gas selectively to a portion of the oxygenator.

18. The system of claim 17, wherein the oxygenator comprises sweep gas microtubules in a fiber bundle.

19. The system of claim 18, wherein the means of flowing the sweep gas selectively to a portion of the oxygenator comprises means of flowing the sweep gas selectively to a fraction of the sweep gas microtubules in the oxygenator fiber bundle.

20. A method for reducing gaseous microemboli using the system of claim 17, the method comprising oxygenating the blood in the oxygenator, and selectively flowing the sweep gas to the portion of the oxygenator.

\*   \*   \*   \*   \*